United States Patent [19]
Hosokawa et al.

[11] Patent Number: 5,869,088
[45] Date of Patent: Feb. 9, 1999

[54] TRANSDERMAL ADMINISTRATION PREPARATION OF A 9-AMINOCYCLOPENTA (B) QUINOLINE

[75] Inventors: Yuko Hosokawa, Omiya; Mutsuo Okumura, Kumagaya; Mitsuru Ochiai, Iwatsuki, all of Japan

[73] Assignee: Nikken Chemicals Co., Ltd, Tokyo, Japan

[21] Appl. No.: 817,510

[22] PCT Filed: Oct. 24, 1995

[86] PCT No.: PCT/JP95/02183

§ 371 Date: Apr. 17, 1997

§ 102(e) Date: Apr. 17, 1997

[87] PCT Pub. No.: WO96/12495

PCT Pub. Date: May 2, 1996

[30] Foreign Application Priority Data

Oct. 24, 1994 [JP] Japan .................................. 6-282467

[51] Int. Cl.$^6$ ...................................... A61F 13/00
[52] U.S. Cl. .................. 424/449; 424/448; 514/944; 514/969
[58] Field of Search .................. 424/449, 448; 514/944, 969

[56] References Cited

U.S. PATENT DOCUMENTS

| | | | |
|---|---|---|---|
| 4,550,113 | 10/1985 | Lavretskaya et al. | 514/290 |
| 4,735,953 | 4/1988 | Lavretskaya et al. | 514/313 |
| 5,019,395 | 5/1991 | Mahjour et al. | 424/449 |
| 5,629,007 | 5/1997 | Audia | 424/443 |

FOREIGN PATENT DOCUMENTS

| | | |
|---|---|---|
| 59-55830 | 3/1984 | Japan . |
| 63-22520 | 1/1988 | Japan . |
| 4-89429 | 3/1992 | Japan . |
| 4-338325 | 11/1992 | Japan . |
| 6-247846 | 9/1994 | Japan . |

*Primary Examiner*—D. Gabrielle Brouillette
*Attorney, Agent, or Firm*—Finnegan, Henderson, Farabow, Garrett & Dunner, L.L.P.

[57] ABSTRACT

A transdermal administration preparation containing a 9-aminocyclopenta(b)quinoline, preferably 9-amino-2, 3,5, 6,7,8-hexahydro-1H-cyclopentane(b)quinoline or its hydrochloride, as an active ingredient and the following transdermal absorption enhancer, that is, at least one compound selected from the group consisting of fatty acids, fatty acid esters, and alcohols, preferably the glyceride of a saturated fatty acid having 6 to 12 carbon atoms.

12 Claims, No Drawings

TRANSDERMAL ADMINISTRATION PREPARATION OF A 9-AMINOCYCLOPENTA (B) QUINOLINE

This application is a 371 of PCT/JP95/02183, filed Oct. 24, 1995.

TECHNICAL FIELD

The present invention relates to a transdermal administration preparation, more specifically a transdermal administration preparation containing a 9-amino-cyclopenta(b)quinoline as an active ingredient.

BACKGROUND ARTS 9-aminocyclopenta(b)quinolines, in particular, 9-amino-2,3,5,6,7,8-hexahydro-1H-cyclopenta(b)quinoline or its salts, as disclosed in Japanese Examined Patent Publication (Kokoku) No. 63-35611 and Japanese Examined Patent Publication (Kokoku) No. 3-54922, are compounds useful as medicines for the treatment of Alzheinier's disease and other dementia and as medicines for the treatment of peripheral nerve-muscle transmission disorders. It is described that these compounds are to be administered to patients orally or by injection etc. to achieve the desired pharmaceutical effects.

Japan has experienced a sharp rise in diseases peculiar to the aged along with the rapid aging of its population. In particular, senile dementia, especially Alzheimer's disease, have as major symptoms impairment of memory, disorientation, dyslogia, etc. In addition, many patients exhibit abnormal behavior such as poriomania. Further, some exhibit symptoms such as hallucinations or delusions. Therefore, the burden on the family members or medical personnel caring for them is high. Measures against this are becoming an important national issue.

Patients suffering from dementia, however, are unable in practice to control the frequency or amount of ingestion of a drug on their own volition even looking at a single administration of a drug. Further, even if a doctor or family member instructs the patients to take the medication, they often cannot understand the instructions or else will not follow the instructions even if understanding them. This is a major hurdle in treatment. Further, the aged generally have reduced swallowing power and, therefore, quite a few patients complain of suffering when ingesting solids such as tablets.

In this way, in patients suffering from senile dementia, oral administration of a drug often becomes difficult along with the progression of the disease. In this case, normally the drug is administered by non-oral methods, that is, injection etc., but in this case it is essential that this be done by a doctor or other expert. On top of this, patients suffering from senile dementia differ from other patients in that there are a large number of patients fared for at home where trips to the hospital are difficult, therefore it is becoming urgent to find a method of administration of drugs effective for these patients as well.

In view of this situation, in recent years, the transdermal method of administration has been studied in the field of dementia. For example, Japanese Unexamined Patent Publication (Kokai) No. 61-186317 and Japanese Unexamined Patent Publication (Kokai) No. 4-338325 propose transdermal administration preparations containing as an active ingredient tetrahydroaminoacridine etc. known as an antidementia drug.

That is, Japanese Unexamined Patent Publication (Kokai) No. 61-186317 discloses a transdermal absorption preparation composition (for treatment of dementia) comprising a basic drug composed of a combination of a cholinergic agent or anticholinergic agent and a low molecular weight fatty acid.

Further, Japanese Unexamined Patent Publication (Kokai) No. 4-338325 discloses a transdermal absorption preparation of a two-layer composite laminate comprising a silicone elastomer and a large-pore polyethylene slab and containing tetrahydroaminoacridine etc. as a drug.

However, these known preparations have the defects that the tetrahydroaminoacridine used as the active ingredient has strong side effects on the liver and further the frequency of occurrence of these side effects is extremely high, therefore cannot be safety used for patients suffering from dementia. No satisfactory therapeutic agent, has yet been found.

DISCLOSURE OF INVENTION

In view of the above situation, the present inventors engaged in various studies to develop a practical and safe antidementia drug of a transdermal administration type and, as a result, found that a 9-aminocyclopenta(b)quinoline, in particular, 9-amino-2,3,5,6,7,8-hexahydro-1H-cyclopenta(b)quinoline, has an extremely superior action against dementia and is extremely high in safety with only very slight side-effects. They further engaged in detailed studies on the absorption from the skin (skin permeation) and, as a result, found that these drugs surprisingly are absorbed to a certain extent even transdermally and further if joint use is made of a specific transdermal absorption enhancer, a concentration in the blood of a level sufficient for exhibiting a pharmaceutical effect as a drug for treating dementia is obtained, whereby the present invention has been completed.

Accordingly, the main object of the present invention is to provide a transdermal administration preparation containing a 9-aminocyclopenta(b)quinoline as an active ingredient.

Another object of the present invention is to provide a transdermal administration type antidementia drug containing a 9-aminocyclopenta(b) quinoline and a transdermal absorption enhancer.

A further object of the present invention is to provide a safe and practical transdermal absorption type antidementia drug.

Other objects of the present invention will become clearer from the following explanation in this description.

In accordance with the present invention, there is provided a transdermal administration preparation comprising a 9-amitiocyclopenta(b)quinoline, as an active ingredient, and a transdermal absorption enhancer formulated in an external base (composition).

BEST MODE FOR CARRYING OUT THE INVENTION

The preferable 9-aminocyclopenta(b)quinoline to be used as the active ingredient in the present invention is 9-amino-2,3,5,6,7,8-hexahydro-1H-cyclopenta(b)quinoline of a structure with a hydrated skeleton portion or a compound of this compound with the 1-position and/or 8-position substituted with a hydroxyl group. Particularly preferred is 9-amino-2,3,5,6,7,8-hexahydro-1H-cyclopenta(b)quinoline or its pharmaceutically acceptable salt. As the salt, a hydrochloride, sulfate, phosphate, fumarate, succiniate, or other pharmaceutically acceptable inorganic acid salt or organic acid salt is used, among which, a hydrochloride and its hydrate, for example, in the case of a 9-amino-2,3,5,6, 7,8-hexahydro-1H-cyclopenta(b)quinoline, a hydrochloride monohydrate is preferred.

The amounts of the active ingredient (drug) contained in the preparation need be only an amount sufficient for manifesting the desired pharmaceutical effect. It differs according to the administered preparation, the type and amount used of the transdermal absorption enhancer, the type of the drug used, etc., but normally a content equivalent to 1 to 30% by weight in the preparation is used. In a transdermal administration preparation, generally the higher the concentration (amount of use) of the drug in the preparation, the greater the amount of permeation through the skein that can be expected. The residual amount of the drug in the preparation after use of the preparation, however, increases in proportion to this, and therefore, a content (amount of use) of the drug in the transdermal absorption preparation in the range described above is preferred.

As the transdermal absorption enhancer, a fatty acid, fatty acid ester, alcohol, etc. may be used.

As the fatty acid usable as the transdermal absorption agent, a saturated or unsaturated fatty acid having 12 to 18 carbon atoms, for example, lauric acid, myristic acid, oleic acid, etc. is preferred. For example, a fatty acid having a small number of carbon atoms, for example 1 to 4 carbon atoms, is not suitable due to the stench and skin irritation caused.

As the fatty acid ester usable as the transdermal absorption agent, a medium chain fatty acid glyceride or medium chain fatty acid glycol monoester (e.g., ethylene glycol monocaprylate, propylene glycol monocaprylate, etc.) is preferred, among which, a saturated fatty acid monoglyceride having 6 to 12 carbon atoms, for example, caprylic acid monoglyceride, capric acid monoglyceride, lauric acid monoglyceride, etc. are particularly preferred. These saturated fatty acid monoglycerides can be easily available from the commercial products, such as "Stinsoft 700P-2" (caprylic acid monoglyceride, product of Taiyo Kagaku K.K.)

As the alcohol usable as the transdermal absorption agent, a saturated or unsaturated alcohol having 4 to 12 carbon atoms, for example, octyl alcohol, lauryl alcohol, etc. is preferred.

The amount of the transdermal absorption enhancer contained in the preparation is not necessarily fixed due to the different types of external bases used, but normally is in the range of 1 to 50% by weight.

Further, these transdermal absorption enhancers may be used in any appropriate mixture thereof, if necessary.

In addition, in the present invention, as solution adjuvants, ethanol, propanol, and other lower alcohols may be used.

As explained above, in the transdermal administration preparation of the present invention, combined use of the active ingredient and a transdermal absorption enhancer enables an extremely advantageous effect to be obtained, but in the specific application for a preparation, it is possible to select from any of various forms of preparations expected to give a pharmaceutical effect by transdermal absorption depending upon the purpose, for example, an ointment preparation, cream preparation, gel preparation, cataplasma preparation, plaster preparation (tape preparation, patch preparation, etc.), use an external base and other additives suited to the desired preparation, and prepare the same by an ordinary method, for example, a method described in the general provisions of preparations of the 12th edition of the Japan Pharmacopeia so as to make various forms of preparations.

In the present invention, as the external base for blending the active ingredient and the transdermal absorption accelerator, a substance normally meeting the requirements of the form of the preparation aimed at may be used, but basically the known substances usually used as substrates for these preparations in the past are used.

For example, in the case of an ointment preparation, the substrate used may be vaseline, oleaginous ointment base, a lanolin and also an animal or plant oil, natural wax, other wax, or hydrates of the same.

Further, when adjustment of the viscosity is required, liquid paraffin, paraffin wax, microcrystalline wax, etc. may be suitably used.

In the case of a cream preparation, the base used is a vaseline, an ester, triglyceride, straight (chain higher alcohol (cetanol, stearyl alcohol, etc. of a chain length of 14 to 18 carbons or so) etc. In this case, the emulsification and physical stability may be maintained by further using a non-ionic surfactant, for example, a sorbitan fatty acid ester, sorbitol fatty acid ester, polyoxyethylene fatty acid ester, polyoxyethylene alkyl ether, polyoxyethylene hardened castor oil derivative, polyoxyethylene potyoxypropylene alkyl ether, etc. in the case of a gel preparation, the base used for an oil-based gel and an aqueous gel differ, balt in the case of an oil-based gel, a liquid oil (including hydrocarbons and esters) is gelated using magnesium stearate, a fatty acid dextran ester, or other gelation agent. In the case of an aqueous gel, a carboxyvinyl polymer, hydroxypropylcellulose, polyvinyl alcohol, aluminum hydroxide, bentonite, or other gelation agent may be used.

In the case of a cataplasma preparation, the substrate used may be gelatin, sodium polyacrylate, polyvinyl alcohol, or polyvinylpyrrolidone.

In the case of a plaster preparation, in the case of either a tape preparation or a patch preparation, the base used may be a natural rubber, synthetic isoprene rubber, or other rubber family adhesive or polyacrylate ester or other polymer acrylic family adhesive and dimethylsiloxane and other silicone family adhesive etc. comprised of polymers. Further, polyethylene terephthalate film is used as a support.

As explained above, in the transdermal administration preparation of the present invention, it is possible to use various substances as the external base, but it is also possible to suitably add into the preparations, when needed, arabia gum, lecithin, glycerin, propylene glycol, and other emulsifiers, suspension agents, humectants, and other additives.

The transdermal administration preparation of the present invention thus prepared is administered to patients according to ordinary methods in accordance with these forms. The dosage is the same as in the past and depends on the form etc., but in general is about 1 to 1,000 mg/day active ingredient for adults.

EXAMPLES

The present invention will now be explained in further detail with reference to Examples, but the present invention is not limited to these Examples and various modifications are possible. Further, in the following Examples and Test Examples, the drug (active ingredient) used, unless specialty otherwise mentioned, was all 9-amino-2,3,5,6,7,8-hexahydro-1H-cyclopenta(b)quinoline hydrochloride monohydrate (9ACQ).

Example 1 (Aqueous Gel Preparation)

0.8 g of hydroxypropylcellulose was added to and dissolved in 20 ml of 40% by weight ethanol. 1 g of caprylic acid monoglyceride and 6 g of a drug (9ACQ) were added to this and stirred well. The mixture was allowed to stand over night in a refrigerator to obtain a aqueous gel preparation.

Example 2 (Cream Preparation)

The ingredients other than the drug and purified water were mixed according to the following formulation. The drug was dissolved in the purified water and added into the mixture which was then stirred and emulsified to obtain a cream preparation.

| | |
|---|---|
| 9ACQ | 1 g |
| White vaseline | 15 g |
| Liquid paraffin | 5 g |
| Cetanol | 5 g |
| Stearyl alcohol | 5 g |
| Polyoxyethylene cetyl ether | 5 g |
| Oleic acid | 10 g |
| Purified water | q.s. |
| Total | 100 g |

Example 3 (Cataplasma Preparation)

The gelatin and purified water were mixed according to the following formulation and then warmed to 70° C. to dissolve the gelatin. A mixture of the zinc oxide, glycerol, sorbitol, and lauryl alcohol was added to the solution which was then mixed well.

Next, sodium polyacrylate and sodium carboxymethylcellulose were added with vigorous stirring. A mixture of the menthol, camphor, and drug was then added to this mixture.

The resultant mixture was kneaded well and spread over a nonwoven fabric. The surface of the ointment was covered by a polyethylene film. The resultant product was cut into suitable sizes to obtain cataplasma preparations.

| | |
|---|---|
| 9ACQ | 1 g |
| Gelatin | 10 g |
| Zinc oxide | 10 g |
| Glycerol | 10 g |
| Sorbitol | 10 g |
| Lauric alcohol | 10 g |
| Sodium polyacrylate | 5 g |
| Sodium carboxymethylcellulose | 5 g |
| Menthol | 2 g |
| Camphor | 1 g |
| Purified water | q.s. |
| Total | 100 g |

Example 4 (Ointment Preparation)

White vaseline, stearyl alcohol, polyoxyethylene hydrogenated castor oil 60, glycerol monostearate, and oleic acid were taken according to the following formulation, mixed on a water bath, heated to dissolve, and held at about 75° C. (Solution 1). Separately, methyl para-oxybenzoate, propyl para-oxybenzoate, and propylene glycol were mixed, then purified water was added and the resultant mixture warmed to about 75° C. (solution 2) and the drug was dissolved in warmed purified water (solution 3).

The solution 2 and solution 3 were gradually added to the solution 1 with stirring, then the warming was stopped. The stirring was continued until solidifying to obtain the ointment preparation.

| | |
|---|---|
| 9ACQ | 1 g |
| White vaseline | 25 g |
| Stearyl alcohol | 20 g |
| Propylene glycol | 12 g |
| Polyoxyethylene hardened castor oil 60 | 4 g |
| Glycerol monostearate | 1 g |
| Methyl para-oxybenzoate | 0.1 g |
| Propyl para-oxybenzoate | 0.1 g |
| Oleic acid | 5 g |
| Purified water | q.s. |
| Total | 100 g |

Example 5 (Tape Preparation)

1 g of a drug (9ACQ) and 5 g of an acrylic adhesive Polysic 310-S (commercial product of Sanyo Kasei Kogyo) were added to 3 ml of ethyl acetate and stirred well (solution 1). Further, 0.03 g of the cross-linking agent isophorone isocyanate was dissolved in 0.5 ml ethyl acetate (solution 2). 3 g of caprylic acid monoglyceride was suspended in 6 ml of ethyl acetate (solution 3). Solution 2 and solution 3 were mixed into solution 1 and stirred well to obtain a viscous solution. This solution was coated on a substrate (polyethylene terephthalate (PET) film) to give a thickness of about 60 microns and then dried to obtain a tape preparation.

Test Example 1

The preparation (sample F) obtained in the above Example 1 and the samples prepared as explained below were tested for skin permeation using skin excised from the abdomen of hairless rats (male, body weight of 220 g to 250 g).

Preparation of Samples

The samples used in the test, except those obtained from the above Examples, were prepared by the following methods:

Sample A: 1.2 g of 9ACQ and 0.3 g of caprylic acid monoglyceride were placed in 6 ml of water and stirred well to obtain a preparation.

Sample B: 1.2 g of 9ACQ and 0.3 g of capric acid monoglyceride were placed in 6 ml of water and stirred well to obtain a preparation.

Sample C: 1.2 g of 9ACQ was placed in 6 ml of water and stirred well to obtain a preparation.

Sample D: 1.4 g of tetrahydroaminoacridine hydrochloride (THA) and 0.3 g of caprylic acid monoglyceride were placed in 6 ml of water and stirred well to obtain a preparation.

Sample E: 1.4 g of THA was placed in 6 ml of water and stirred well to obtain a preparation.

Sample G: 0.8 g of hydroxypropylcellulose was added to and dissolved in 20 ml of 40% ethanol. 6 g of 9ACQ was added to this mixture and the mixture was stirred well. The mixture was allowed to stand overnight in a refrigerator to obtain a water-based gel preparation.

Test Method

The test was carried out using a 2-chamber diffusion cell of the flow-through type (effective area of 1 cm$^2$ and volume of 2.5 ml), setting different preparations at the donor side (stratum corneum layer side), placing normal saline at the receiver side, quantizing the amount of the drug moving from the samples (preparations) through the skin to the receiver side by high pressure liquid chromatography, and finding the skin permeation rates based on the same. The results are shown in Table 1.

TABLE 1

Skin Permeation of Various Preparations

| Sample | Drug | Composition of preparation | Skin permeation rate* ($\mu g/cm^2/hr$) |
|---|---|---|---|
| Invention | | | |
| A | 9ACQ | Caprylic acid monoglyceride, water | 2155 ± 434 |
| B | 9ACQ | Capric acid monoglyceride, water | 1912 ± 768 |
| Control | | | |
| C | 9ACQ | Water | 35 ± 11 |
| D | THA | Caprylic acid monoglyceride, water | 37 ± 15 |
| E | THA | Water | 3 ± 2 |
| Invention | | | |
| F | 9ACQ | 40% ethanol, caprylic acid monoglyceride, hydroxypropylcellulose | 5254 ± 575 |
| Control | | | |
| G | 9ACQ | 40% ethanol, hydroxypropylcellulose | 12 ± 2 |

Test Example 2

The preparation (sample F) obtained in the above Example 1 and the sample G prepared in Test Example 1 were tested for in vivo skin permeation in hairless rats according to the following test method.

Test Method

The chest portions of hairless rats were shorn and various samples applied. The area of administration of the samples was 1 cm² and the dosage was 2.8 g. The blood was sampled 2, 4, 6, 8, and 24 hours after adherence. The drug was extracted from the serum and was quantized by the CGC/MS method to find the concentration in the blood. The results are shown in Table 2.

TABLE 2

In Vivo Skin Permeation in Hairless Rats

| Adherence time | Concentration in blood (ng/ml) | |
|---|---|---|
| (hr) | Ex. 1 | Sample G |
| 2 | 192 ± 51 | 35 ± 6 |
| 4 | 924 ± 413 | 64 ± 19 |
| 6 | 2943 ± 1006 | 101 ± 34 |
| 8 | 3796 ± 965 | 138 ± 58 |
| 24 | | 34 ± 16 |

*Figures are shown as mean values ± S.E. of four examples.

Test Example 3

The samples prepared as described below were tested by methods similar to those of Test Example 1. The results are shown in Table 3.

Sample H: 1.2 g of 9ACQ and 0.3 g of lauric acid were placed in 6 g of 40% by weight ethanol and stirred well to obtain a preparation.

Sample I: The same procedure as the method of preparation of sample H was followed to obtain a preparation except that the lauric acid was made oleic acid.

Sample J: The same procedure as the method of preparation of sample H was followed to obtain a preparation except that the lauric acid was made octanol.

Sample K: 2.4 g of 9ACQ and 0.3 g of caprylic acid monoglyceride were placed in 6 g of 40% by weight ethanol and stirred well to obtain a preparation.

Sample L: 1.2 g of 9ACQ was placed in 6 g of 40% by weight ethanol and stirred well to obtain a preparation.

Sample M: 2.4 g of THA and 0.3 g of caprylic acid monoglyceride were inserted into 6 g of 40% by weight ethanol and stirred well to obtain a preparation.

TABLE 3

Skin Permeation of Various Preparations

| Sample | Drug | Composition of preparation | Skin permeation rate* ($\mu g/cm^2/hr$) |
|---|---|---|---|
| Invention | | | |
| H | 9ACQ | Lauric acid, 40% ethanol | 9776 ± 83 |
| I | 9ACQ | Oleic acid, 40% ethanol | 6287 ± 198 |
| J | 9ACQ | Octanol, 40% ethanol | 9686 ± 505 |
| K | 9ACQ | Caprylic acid monoglyceride, 40% ethanol | 18212 ± 2477 |
| Control | | | |
| L | 9ACQ | 40% ethanol | 59 ± 29 |
| M | THA | Caprylic acid monoglyceride, 40% ethanol | 293 ± 57 |

*Figures are shown as mean value ± S.E. of three examples.

INDUSTRIAL AVAILABILITY

According to the transdermal administration preparation of the present invention, it is possible for a care-giver to easily administer a drug to a patient suffering from dementia and further the required concentration of the drug administered in the blood is maintained over a long period, and therefore, present invention is extremely useful for patients suffering from dementia for which administration of drugs is difficult.

We claim:

1. A transdermal administration preparation comprising from 1 to 30% by weight of a 9-aminocyclopenta(b) quinoline or a pharmaceutically acceptable salt thereof as an active ingredient and at least one transdermal absorption enhancer selected from the group consisting of fatty acids, fatty acid esters and alcohols.

2. A transdermal administration preparation as claimed in claim 1, wherein the active ingredient is 9-amino-2,3,5,6,7,8-hexahydro-1H-cyclopenta(b)quinoline or its pharmaceutically acceptable salt.

3. A transdermal administration preparation as claimed in claim 2, wherein the active ingredient is 9-amino-2,3,5,6,7,8-hexahydro-1H-cyclopenta(b)quinoline hydrochloride monohydrate.

4. A transdermal administration preparation as claimed in any one of claims 1–3, wherein the transdermal absorption enchancer is a fatty acid.

5. A transdermal administration preparation as claimed in claim 4, wherein the fatty acid is a saturated or unsaturated fatty acid having 12 to 18 carbon atoms.

6. A transdermal administration preparation as claimed in any one of claims 1–3, wherein the transdermal absorption enhancer is a fatty acid ester.

7. A transdermal administration preparation as claimed in claim 6, wherein the fatty acid ester is a glyceride of a medium chain fatty acid.

8. A transdermal administration preparation as claimed in claim 7, wherein the glyceride of the medium chain fatty acid is a monoglyceride of a saturated fatty acid having 6 to 12 carbon atoms.

9. A transdermal administration preparation as claimed in any one of claims 1–3, wherein the transdermal absorption enhancer is an alcohol.

10. A transdermal administration preparation as claimed in claim 9, wherein the alcohol is a saturated or unsaturated alcohol having 4 to 12 carbon atoms.

11. A transdermal administration preparation as claimed in any one of claims 1 to 3, wherein the transdermal administration preparation is one form selected from the group consisting of an ointment, cream, gel, and cataplasma preparation.

12. A transdermal administration preparation as claimed in any one of claims 1 to 3, wherein the transdermal administration preparation is a tape or patch preparation.

* * * * *